US012082801B2

(12) United States Patent
Dooney, Jr. et al.

(10) Patent No.: US 12,082,801 B2
(45) Date of Patent: Sep. 10, 2024

(54) METHOD OF TISSUE REPAIR

(71) Applicant: Arthrex, Inc., Naples, FL (US)

(72) Inventors: Thomas Dooney, Jr., Naples, FL (US); Peter J. Dreyfuss, Naples, FL (US); Patrick J. Denard, Jacksonville, OR (US)

(73) Assignee: Arthrex, Inc., Naples, FL (US)

( * ) Notice: Subject to any disclaimer, the term of this patent is extended or adjusted under 35 U.S.C. 154(b) by 687 days.

(21) Appl. No.: 16/902,743

(22) Filed: Jun. 16, 2020

(65) Prior Publication Data

US 2021/0386418 A1  Dec. 16, 2021

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0404* (2013.01); *A61B 2017/0464* (2013.01); *A61F 2002/0852* (2013.01); *A61F 2002/0888* (2013.01)

(58) Field of Classification Search
CPC ............ A61F 2/0811; A61F 2002/0852; A61F 2002/0888; A61F 2002/0858; A61F 2002/0882; A61B 17/0401; A61B 2017/0409; A61B 2017/044; A61B 2017/0445; A61B 2017/0406; A61B 2017/06185; A61B 2017/0412; A61B 2017/0458; A61B 2017/0414; A61B 2017/0464; A61B 2017/0477; A61B 17/0466; A61B 17/0469; A61B 17/0485; A61B 17/0487; A61B 17/06166; A61B 2017/0404; A61B 2017/0417; A61B 2017/0448; A61B 2017/0496; A61B 17/0482; A61B 17/06066; A61B 2017/0427; A61B 2017/042; A61B 2017/0419; A61B 2017/0408; A61B 2017/0403; A61B 2017/0475
See application file for complete search history.

(56) References Cited

U.S. PATENT DOCUMENTS

| | | | | |
|---|---|---|---|---|
| 4,823,794 | A | * | 4/1989 | Pierce ................ A61B 17/0401 606/232 |
| 6,066,160 | A | * | 5/2000 | Colvin ............... A61B 17/0487 606/232 |
| 6,475,230 | B1 | * | 11/2002 | Bonutti .............. A61B 17/0401 606/232 |
| 8,088,130 | B2 | | 1/2012 | Kaiser et al. |
| 8,118,835 | B2 | | 2/2012 | Weisel et al. |
| 10,368,856 | B2 | | 8/2019 | Stone et al. |
| 10,542,967 | B2 | | 1/2020 | Kaiser et al. |
| 2009/0082805 | A1 | * | 3/2009 | Kaiser ............. A61B 17/06166 606/228 |
| 2011/0245850 | A1 | * | 10/2011 | van der Burg ......... A61B 90/39 606/145 |

(Continued)

*Primary Examiner* — Katherine M Shi
(74) *Attorney, Agent, or Firm* — Blank Rome LLP

(57) ABSTRACT

A method of tissue repair that includes installing a surgical construct in a bone hole. The surgical construct has a fixation device that is preloaded with a primary flexible strand. After installing the surgical construct in the bone hole, the method includes coupling at least one secondary flexible strand to the primary flexible strand for subsequent use in repairing the tissue.

33 Claims, 9 Drawing Sheets

(56) References Cited

U.S. PATENT DOCUMENTS

| | | | |
|---|---|---|---|
| 2012/0130423 A1* | 5/2012 | Sengun | A61B 17/0401 606/232 |
| 2012/0165864 A1 | 6/2012 | Hernandez et al. | |
| 2014/0249577 A1* | 9/2014 | Pilgeram | A61B 17/0485 606/228 |
| 2015/0173739 A1* | 6/2015 | Rodriguez | A61B 17/0401 606/232 |
| 2015/0173754 A1* | 6/2015 | Norton | A61B 17/0401 606/228 |
| 2017/0035412 A1 | 2/2017 | Dooney, Jr. et al. | |
| 2017/0049432 A1* | 2/2017 | Dooney, Jr. | A61B 17/0487 |

* cited by examiner

METHOD OF TISSUE REPAIR

FIELD OF THE INVENTION

The present disclosure generally relates to surgical methods of tissue repair.

BACKGROUND OF THE INVENTION

When soft tissue, such as a ligament or a tendon, tears or becomes detached from a bone, surgery is usually required to reattach or reconstruct the tissue. A tissue graft may be attached to the bone to facilitate regrowth and permanent attachment. Techniques and devices that have been developed generally involve tying the soft tissue with suture to an anchor, and securing the anchor in a hole provided in the bone tissue.

SUMMARY OF THE INVENTION

The present disclosure provides a method of tissue repair that comprises the step of installing a surgical construct in a bone hole, where the surgical construct includes a fixation device that is preloaded with at least one primary flexible strand, and after installing the surgical construct in the bone hole, coupling at least one secondary flexible strand to the primary flexible strand for subsequent use in repairing the tissue. In an embodiment, either the primary or secondary flexible strand is configured to pass through or extend around tissue.

In certain embodiments of the present disclosure, the secondary flexible strand is different than the primary flexible strand; the secondary flexible strand has a length that is different than a length of the primary flexible strand; the secondary flexible strand is formed of a different material than the primary flexible strand; the primary and secondary flexible strands are formed of the same material; and/or the primary and secondary flexible strands are one of sutures or suture tapes.

In some embodiments of the present disclosure, the secondary flexible strand is separable from the primary flexible strand; the step of coupling the second flexible strand to the primary flexible strand includes slidably coupling the second flexible strand around a segment of the primary flexible strand; the step of coupling the secondary flexible strand to the primary flexible strand includes extending the primary flexible strand through the eyelet of the secondary flexible strand; the secondary flexible strand has a length of suture or suture tape with an eyelet at an end thereof for coupling with the primary flexible strand; the method further comprises the step of coupling another secondary flexible strand to the primary flexible strand after the step of installing the surgical construct into the bone hole; and/or the fixation device of the surgical construct is a soft anchor.

In other embodiments, the method further comprises the step of coupling a tissue fixation device to the secondary flexible strand; the method further comprises the step of extending the secondary flexible strand through or around tissue and then tying free ends of the secondary flexible strand; the method further comprises the step of coupling a tissue fixation device to the free ends of the secondary flexible strand; the tissue fixation device is a button and the free ends of the secondary flexible strand extend around or through apertures of the button; and/or the method further comprises the step of coupling at least one of the primary or secondary flexible strands to a second fixation device installed in another bone hole.

The present disclosure may also provide a method of tissue repair that comprises the steps of: installing an surgical construct in a bone hole, the surgical construct having a fixation device that is preloaded with at least one primary flexible strand; creating a tensionable adjustable loop in the primary flexible strand; and after installing the surgical construct in the bone hole, coupling at least one secondary flexible strand to the primary flexible strand for subsequent use in repairing the tissue. In an embodiment, the primary or secondary flexible strand is configured to pass through or extend around tissue.

In some embodiments of the present disclosure, the step of coupling at least one secondary flexible strand to the primary flexible strand occurs before the step of creating the tensionable adjustable loop in the primary flexible strand; and/or the step of coupling at least one secondary flexible strand to the primary flexible strand occurs after the step of creating the tensionable adjustable loop in the primary flexible strand.

In other embodiments of the present disclosure, the method further comprises the step of pulling at least a portion of the secondary flexible strand into the bone hole; the method further comprises the step of anchoring the secondary flexible strand to another bone hole; the method further comprises the step of selecting the secondary flexible strand from a sliding suture or suture tape slidably coupled to the primary flexible strand or a suture or suture tape with an eyelet for coupling to the primary flexible strand; the method further comprises the step of coupling another secondary flexible strand to the primary flexible strand after the step of installing the surgical construct into the bone hole; and/or the secondary flexible strand is separable from the primary strand.

In certain embodiments, the method further comprises the step of coupling either the at least one primary or secondary flexible strand to a second fixation device installed in another bone hole; the method further comprises the step of coupling the at least one secondary flexible strand to a second surgical construct installed in another bone hole; the method further comprising the step of coupling the at least one secondary flexible strand to tissue; and/or the step of coupling the at least one secondary flexible strand to tissue includes coupling a tissue fixation device, such as a button or the like, to the at least one secondary flexible strand.

DETAILED DESCRIPTION

Referring to the figures, the present disclosure relates to methods of tissue repair and surgical constructs 100 used in the methods that provide a back-up or secondary repair mechanism 200 for further manipulation of surgical construct 100, such as for securing the tissue repair and/or for surgical refinement of the tissue repair. The back-up or secondary repair mechanism 200 can be employed during the tissue repair procedure including after the surgical construct 100 has already been anchored into the bone. This provides the surgeon flexibility and options when repairing the tissue, such as when additional securement or precision is needed for the repair. The tissue may be soft tissue, tissue graft, and/or bone.

An exemplary method of the present disclosure includes installing a surgical construct in a bone hole, the surgical construct having a fixation device that is preloaded with at least one primary flexible strand for passing through or extending around tissue; and after installing the surgical construct in the bone hole, coupling at least one secondary flexible strand to the primary flexible strand for subsequent use in repairing the tissue. In another exemplary embodiment, the method may include the step of creating a tensionable, adjustable loop in the primary flexible strand. The primary flexible strand may be any length of flexible strand appropriate for tissue repair, such a suture or suture tape.

Figure 1:
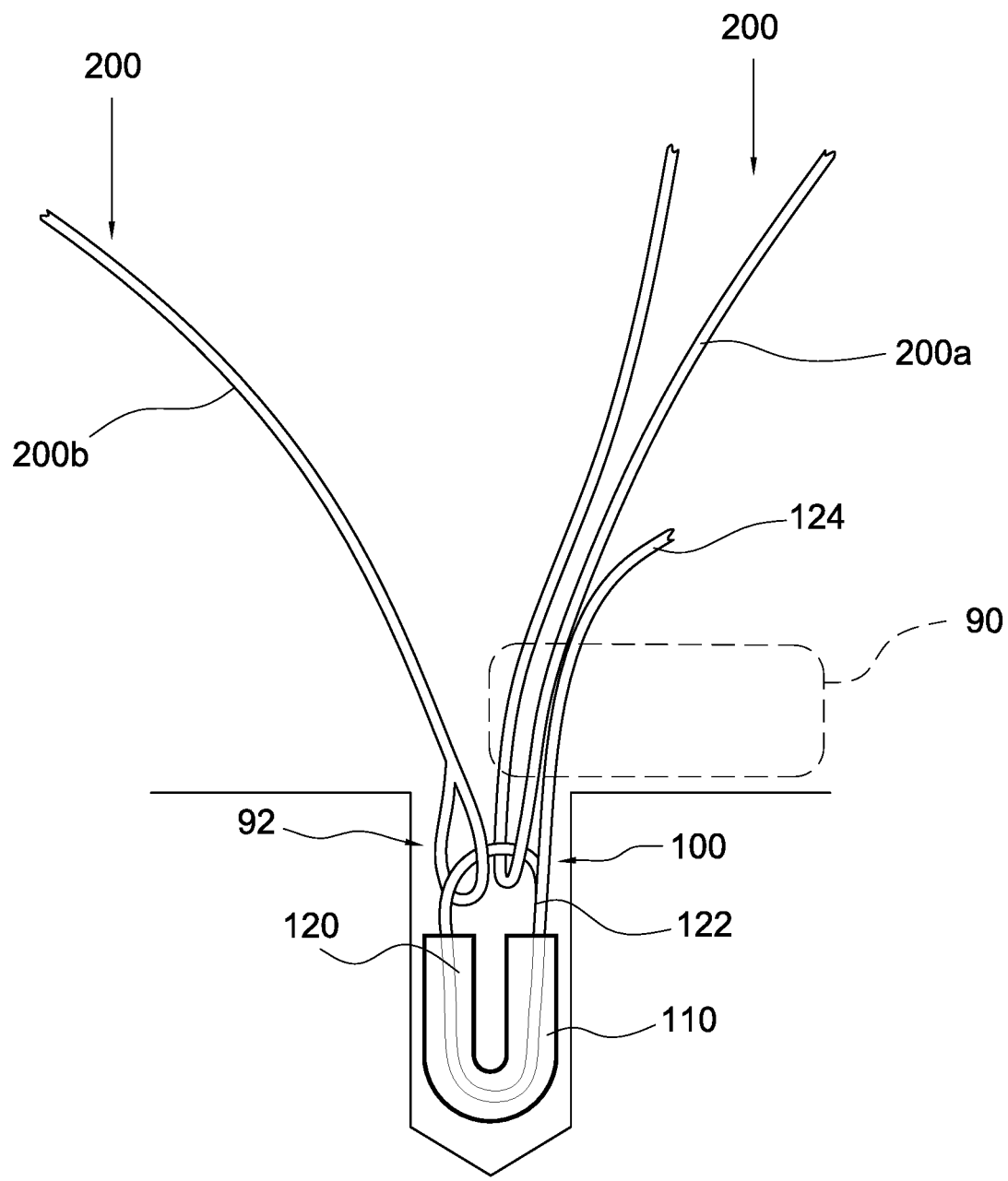
FIG. 1 is an elevational view of an exemplary surgical construct used in an exemplary method of tissue repair of the present disclosure, showing the surgical construct installed in a bone hole.

FIGS. 1 and 2a-2c illustrate an exemplary surgical construct 100 used in accordance with an exemplary method of tissue repair of the present disclosure. Surgical construct 100 generally includes a fixation device 110 and at least one primary repair flexible strand 120 preloaded on fixation device 110. Primary repair flexible strand 120 is configured to extend through or around the tissue 90 for conducting the repair. Fixation device 110 may be any type of soft or hard anchor, such as a soft tubular sheath or a hard anchor body, configured to be installed in and anchored to a pre-drilled bone hole 92. Primary repair flexible strand 120 may extend through fixation device 110, as seen in FIG. 1. Primary repair flexible strand 120 may be any type of flexible strand suitable for surgical tissue repair, such as suture, suture tape, and the like.

Figure 2A:
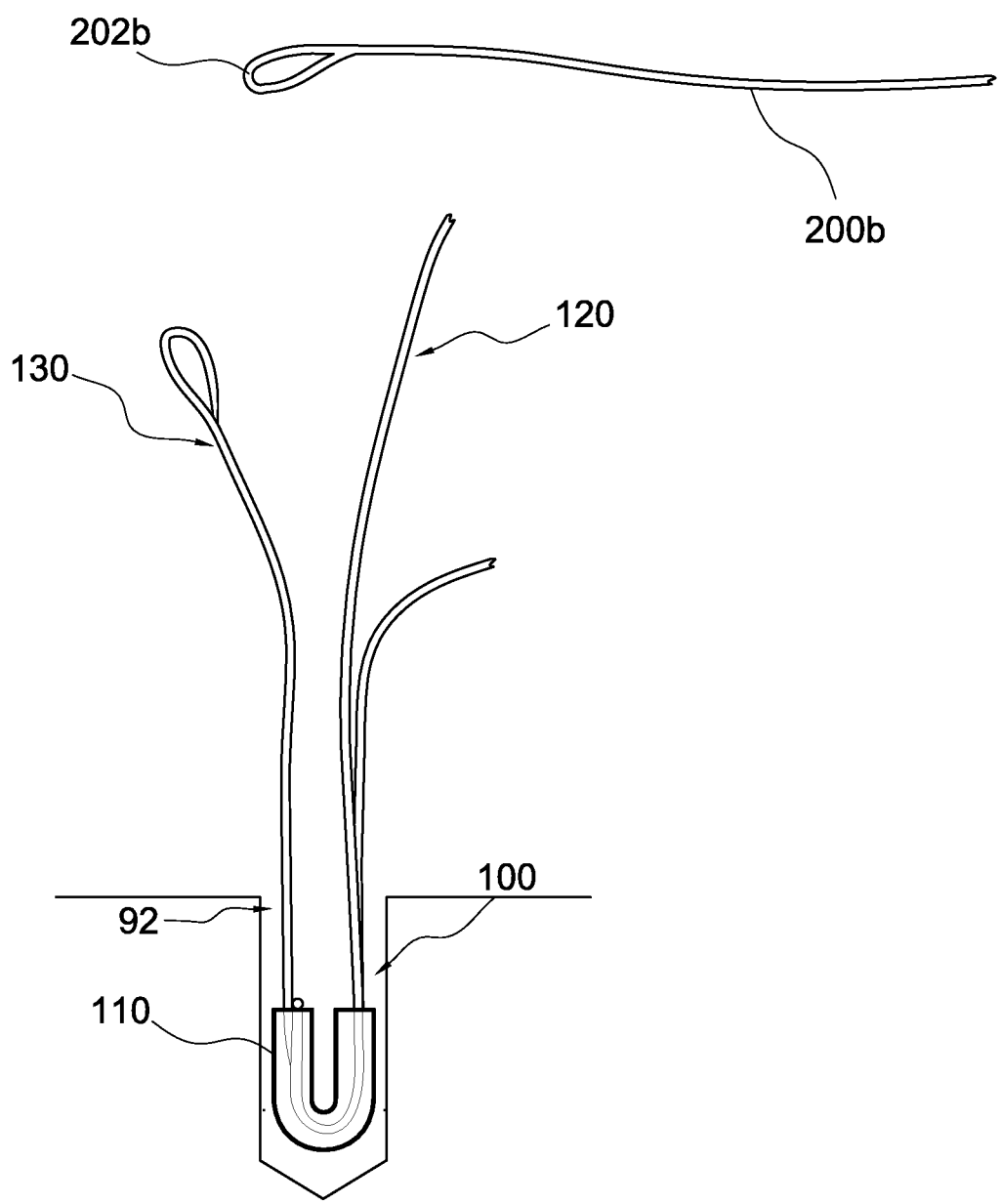
FIGS. 2*a*-2*c* are elevational views of the surgical construct of FIG. 1, illustrating the steps of the exemplary method of tissue repair.
Figure 2B:
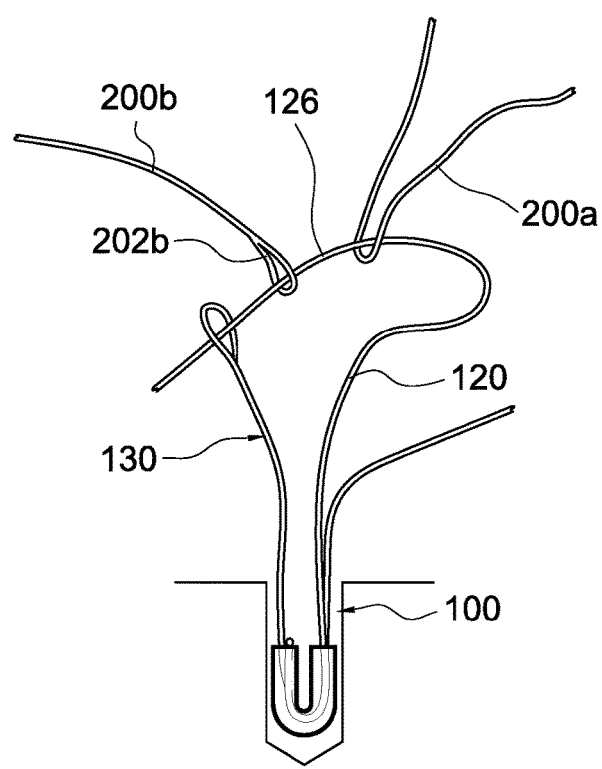
Figure 2C:
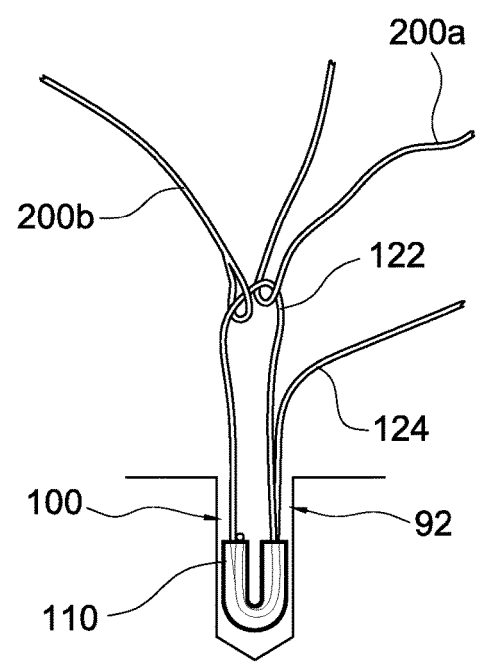
Figure 3A:
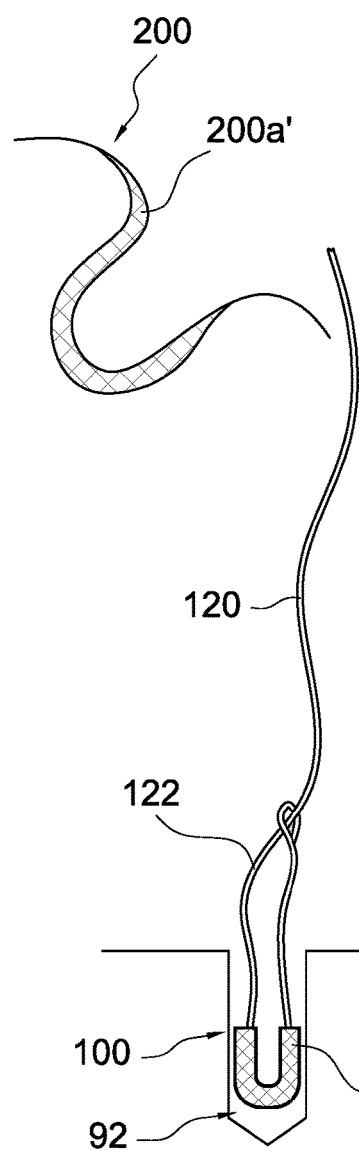
FIGS. 3*a*-3*c* are elevational views of another exemplary surgical construct used in an exemplary method of tissue repair.
Figure 3B:
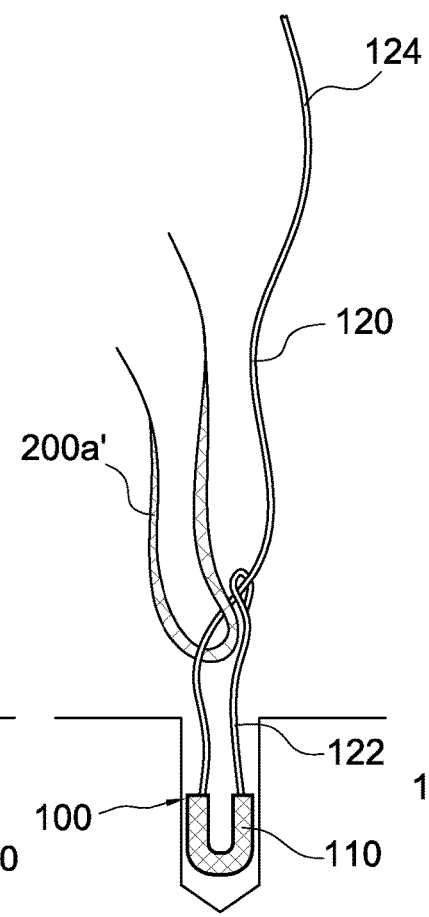
Figure 3C:
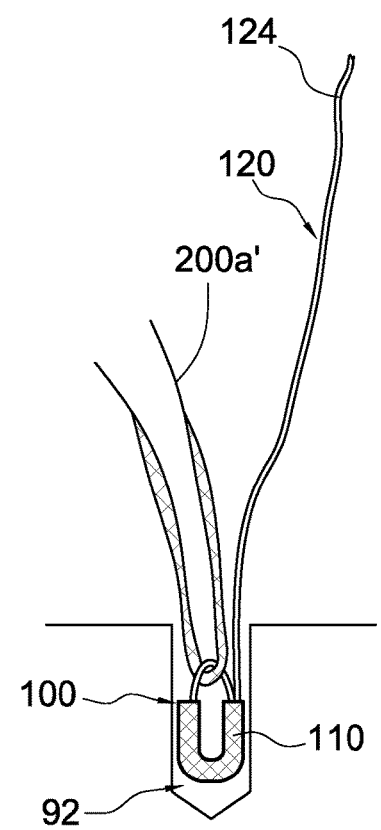

In an embodiment, primary repair flexible strand 120 includes at least one tensionable adjustable loop 122 for use in the tissue repair procedure, the perimeter of which may be reduced by tensioning or pulling on a free end 124 of strand 120. Adjustable loop 122 may be created in primary repair flexible strand 120 in any known matter, such as by threading primary repair flexible strand 120 through itself, e.g. through a splice or passage in the strand, as seen in FIGS. 2a-2c, or by extending a portion of primary repair flexible strand 120 through a fixed loop that is part of or attached to strand 120, as seen in FIGS. 3a-3c. A shuttling or passing device 130 may be used to assist with creating adjustable loop 122, as seen in FIGS. 2a and 2b.

Secondary repair mechanism 200 may be one or more additional or secondary repair flexible strands added to surgical construct 100 after fixation device 100 has been installed and anchored into the bone hole 92. That is, the one or more secondary repair flexible strands 200 are initially separate from surgical construct 100 and primary repair strand 120 before surgical construct 100 has been installed into the bone hole 92, such as seen in FIG. 3a. Once surgical construct 100 is installed into bone hole 92, then the one or more secondary repair flexible strands 200 can be coupled to primary repair strand 120. This leaves the one or more secondary repair flexible strands 200 free for subsequent manipulation and surgical refinement of the repair when needed.

In an embodiment, the one or more secondary repair flexible strands 200 may be a length of flexible strand 200a (FIG. 2c), 200a' (FIG. 3c) that is slidably coupled to primary repair strand 120 such that secondary repair strand 200a, 200a' can be easily added to or removed from surgical construct 100 at any time, including after surgical construct 100 is anchored in bone hole 92. Secondary repair flexible strand 200a, 200a' can be slidably coupled to primary repair flexible strand 120 before adjustable loop 122 is created in strand 120, as seen in FIG. 2b, or slidably coupled after adjustable loop 122 has been created, as seen in FIG. 3b. For example, the length of secondary repair flexible strand 200a, 200a' can be extended around a segment 126 of primary repair strand 120, as seen in FIG. 2b, or extended through adjustable loop 122, to slidably couple secondary repair flexible strand 200a, 200a' to surgical construct 100.

Figure 5:
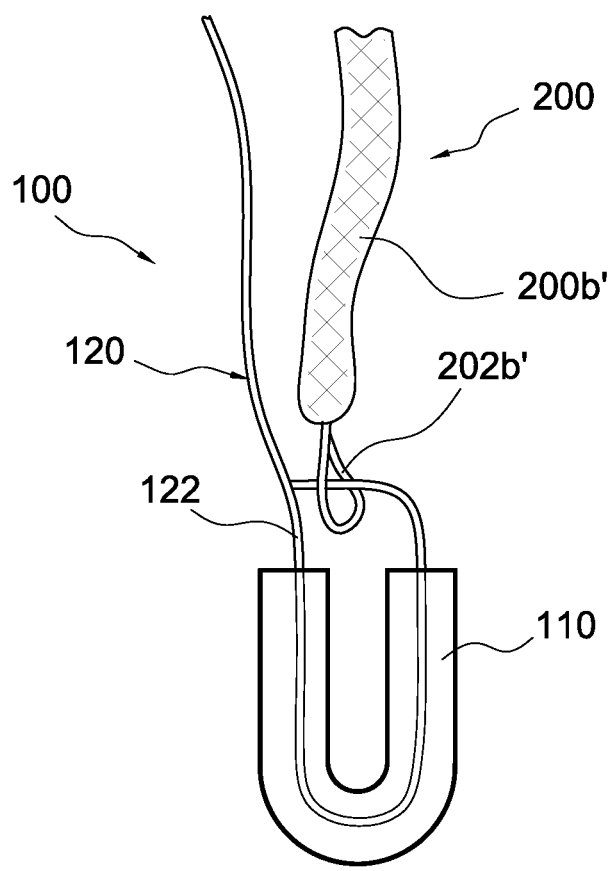
FIG. 5 is a plan view of yet another exemplary surgical construct.

In an embodiment, the one or more secondary repair flexible strands 200 may be a length of flexible strand 200b (FIG. 1), 200b' (FIG. 5) that is coupled to primary repair strand 120 such that secondary repair strand 200b, 200b' cannot be easily removed from surgical construct 100. As such, secondary repair strand 200b, 200b' is added to surgical construct 100 after surgical construct 100 is anchored in bone hole 92 and during or after adjustable loop 122 is created in primary repair strand 120, as seen in in FIG. 2b. For example, secondary repair flexible strand 200b, 200b' may include an eyelet or fixed loop 202b, 202b' positioned at the end of the strand, for example, for coupling to primary repair flexible strand 120 and adjustable loop 122, as seen in FIGS. 1 and 5. A length 128 of primary repair strand 120 may be threaded through eyelet or fixed loop 202b either before or while creating adjustable loop 122, as best seen in FIGS. 2a-2c. Once adjustable loop 122 is created, secondary repair flexible strand 200b, 200b' cannot be easily removed from surgical construct 100 due to the connection with eyelet 202b, 202b', as seen in FIGS. 1 and 5.

Figure 4A:
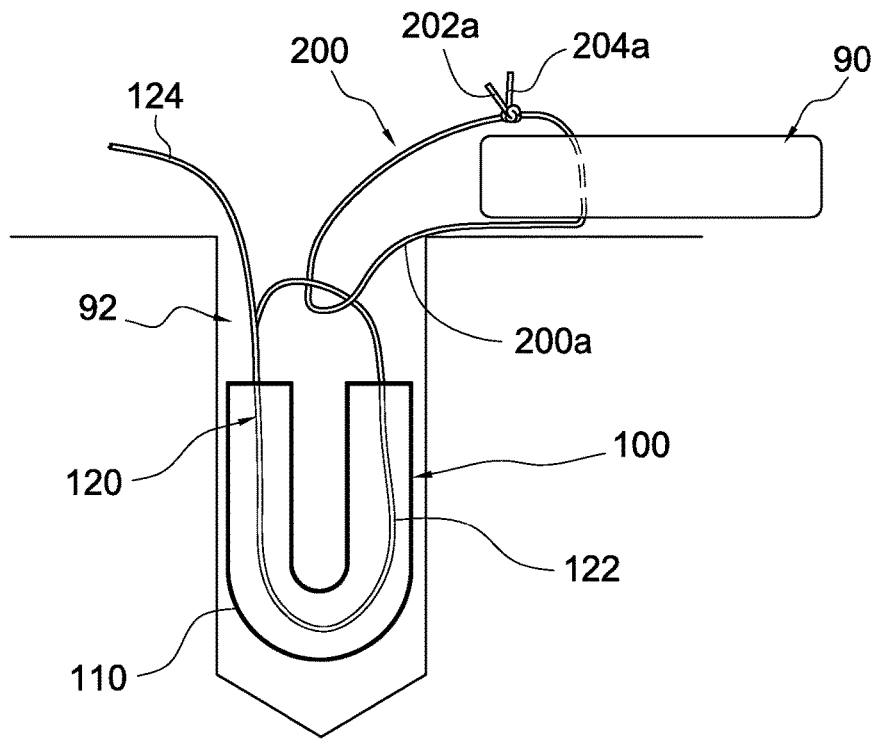
FIGS. 4*a*-4*c* are elevational views of various methods of securing tissue to bone using the surgical construct.
Figure 4B:
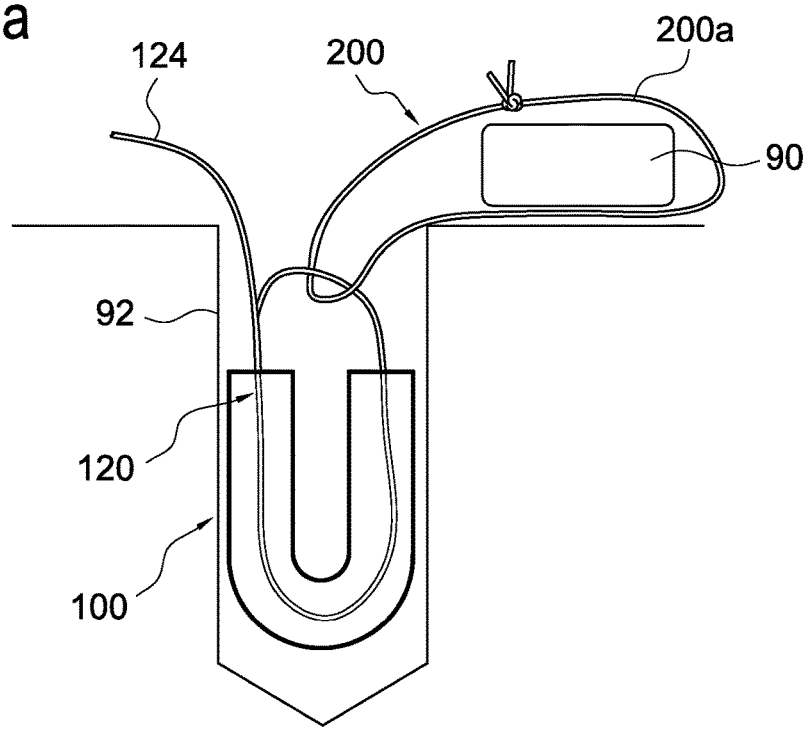
Figure 4C:
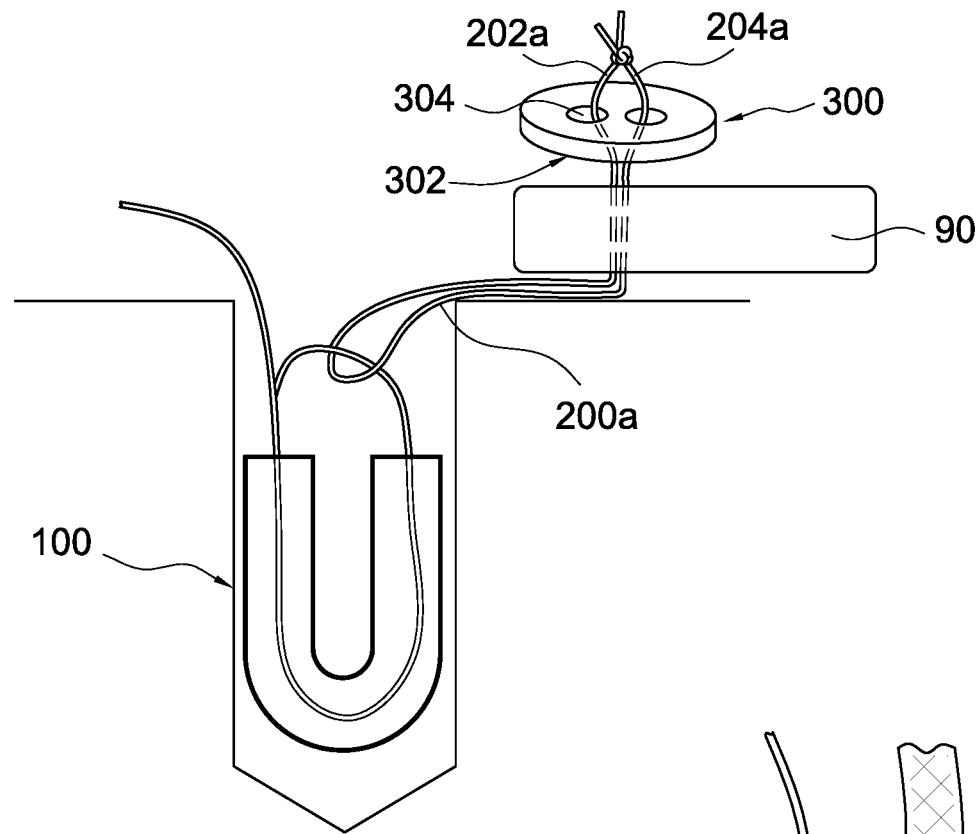

The secondary repair flexible strand 200 may be coupled to the tissue 90, as seen in FIGS. 4a-4c. For example, the secondary repair flexible strand 200a, which is slidably coupled to the primary repair flexible strand 120, can be extended through the tissue 90 (FIG. 4a) or around the tissue 90 (FIG. 4b), and the free ends 202a and 204a can be tied together into a knot to couple the strand 200a to the tissue. As an option, a tissue fixation device 300 (FIG. 4c), such as a button or the like, may be coupled to the strand 200a, which provides a surface area 302 for abutting against the tissue 90 when securing the repair. The free ends 202a and 204a of the strand 200a can be threaded through apertures 304 of the button 300 and then tied together, as seen in FIG. 4c.

Figure 6A:
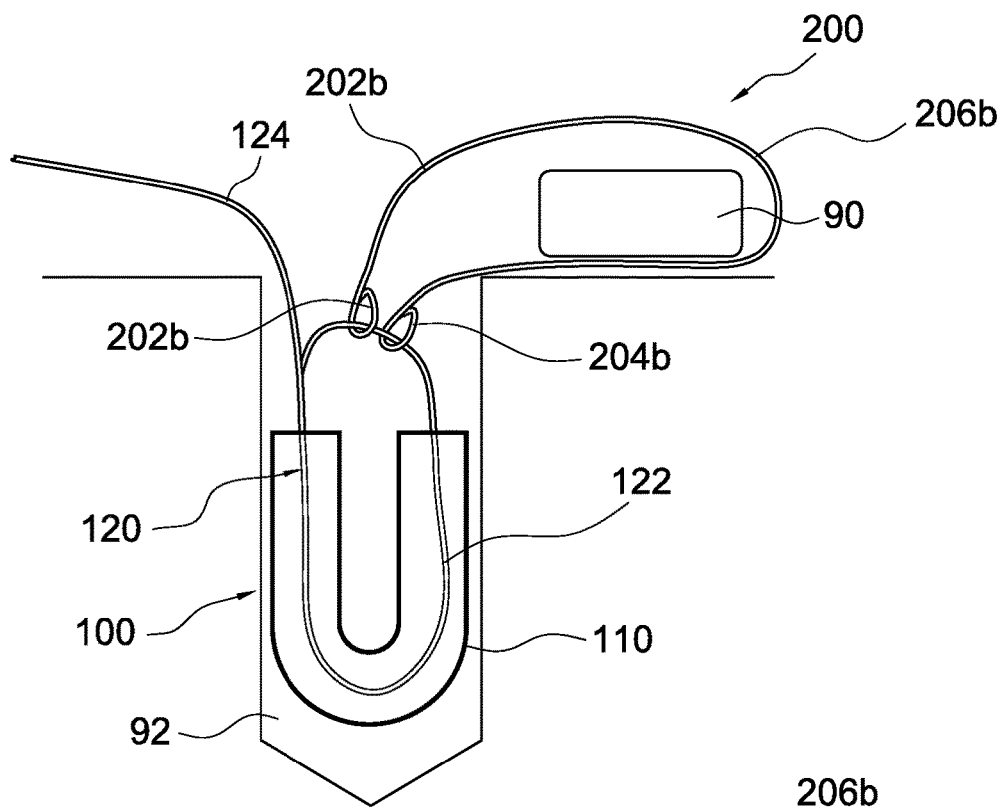
FIGS. 6*a* and 6*b* are each an elevational view of other methods of securing tissue to bone using the surgical construct.
Figure 6B:
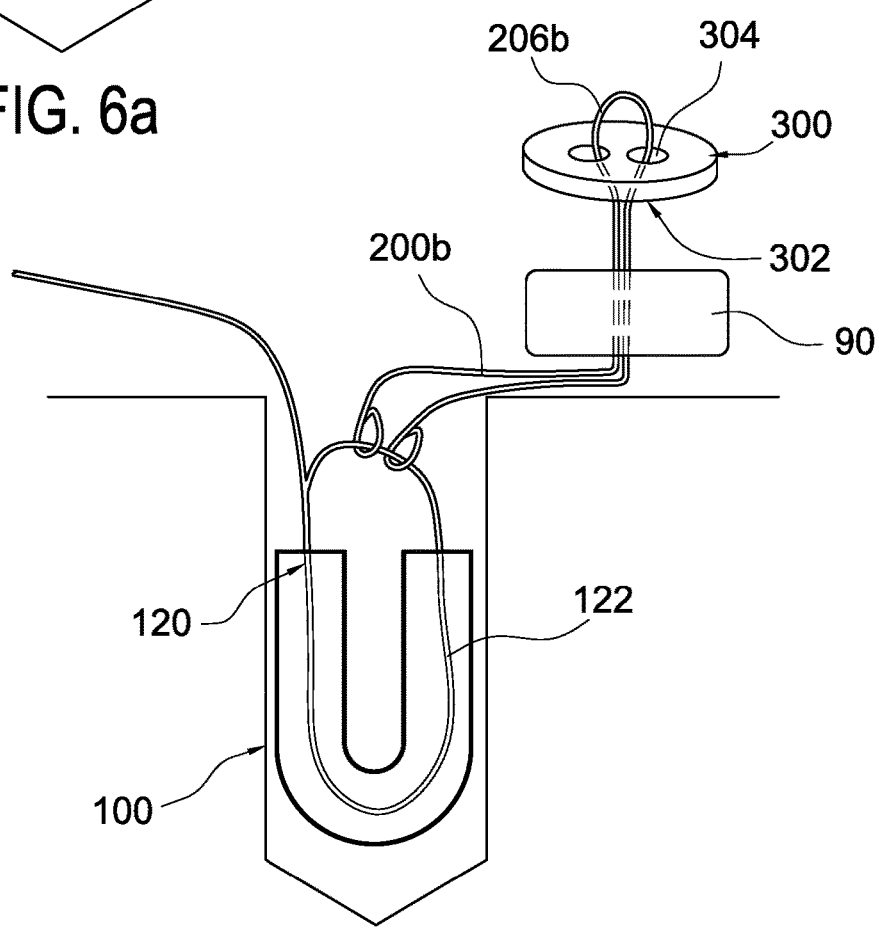

In another example, the secondary repair flexible strand 200b, which includes eyelet 202b that couples to the primary repair flexible strand 120, can be extended around (FIG. 6a) or through (FIG. 6b) the tissue 90 and coupled to the tissue. The secondary repair flexible strand 200b can have a second eyelet 204b at the end of the strand 200b opposite the first eyelet 202b. The second eyelet 204b can be coupled to the primary repair flexible strand 120, e.g. at adjustable loop 122, in a manner similar to eyelet 202b, to create a loop portion 206b in the strand 200b. The loop portion 206b can be extended over the tissue 90, as seen in FIG. 6a. As an option, the loop portion 206b can be coupled to tissue fixation device 300 (FIG. 6b), e.g. a button or the like, for abutting against the tissue 90, when securing the repair. The loop portion 206b can be extended through apertures 304 of the button 300 or can be wrapped around the button 300 to couple the button 300 to the secondary repair flexible strand 200b.

The flexible strands, including primary repair strands 120 and secondary repair strands 200a, 200b, may be any type of flexible strand suitable for surgical tissue repair, such as suture, suture tape, and the like. The flexible strands may have the same, uniform width or may have different widths, and may comprise the same or different materials. Primary repair strands 120 and secondary repair strands 200a, 200b may have similar or different lengths and may be formed of the same or different materials. For example, secondary repair strand 200a, 200b may be a length of suture and secondary repair strand 200a', 200b' may be a length of suture tape.

One or more of secondary repair strands 200a, 200a' may be added to the surgical construct 100; one or more of secondary repair strands 200b, 200b' may be added to the surgical construct 100; or any combination of the secondary repair strands 200a, 200a, 200b, and 200b' may be added to the surgical construct 100 after implanted in bone hole 92.

An exemplary method of tissue repair using surgical construct 100 with the secondary repair mechanism include installing surgical construct 100 in a pre-drilled bone hole 92 and after installing the surgical construct in bone hole 92, coupling at least one secondary repair flexible strand 200a, 200a', 200b, 200b' to primary repair flexible strand 120 for subsequent use in repairing the tissue. The method may also include the step of creating tensionable, adjustable loop 122 in the primary repair flexible strand 120.

The step of coupling the second repair flexible strand 200a, 200a' to the primary repair flexible strand 120 can include slidably coupling the one second flexible strand around a segment 126 of the primary repair flexible strand 120, either before or after adjustable loop 122 is created in strand 120. The step of coupling the secondary flexible strand 200b, 200b' to the primary repair flexible strand 120 includes extending the primary repair flexible strand 120 through the eyelet 202b, 202b' of the secondary repair flexible strand 200b, 200b'.

The method of the present disclosure may optionally include the step of pulling at least a portion of the secondary repair flexible strand 200a, 200a', 200b, 200b' into the bone hole 92, as best seen in FIG. 3c. The method may also optionally include the step of selecting the secondary flexible strand from one of a sliding suture or suture tape 200a, 200a' slidably coupled to the primary repair flexible strand 120 or a suture or suture tape 200b, 200b' with eyelet 202b, 202b' for coupling to the primary repair flexible strand 120.

Figure 7:
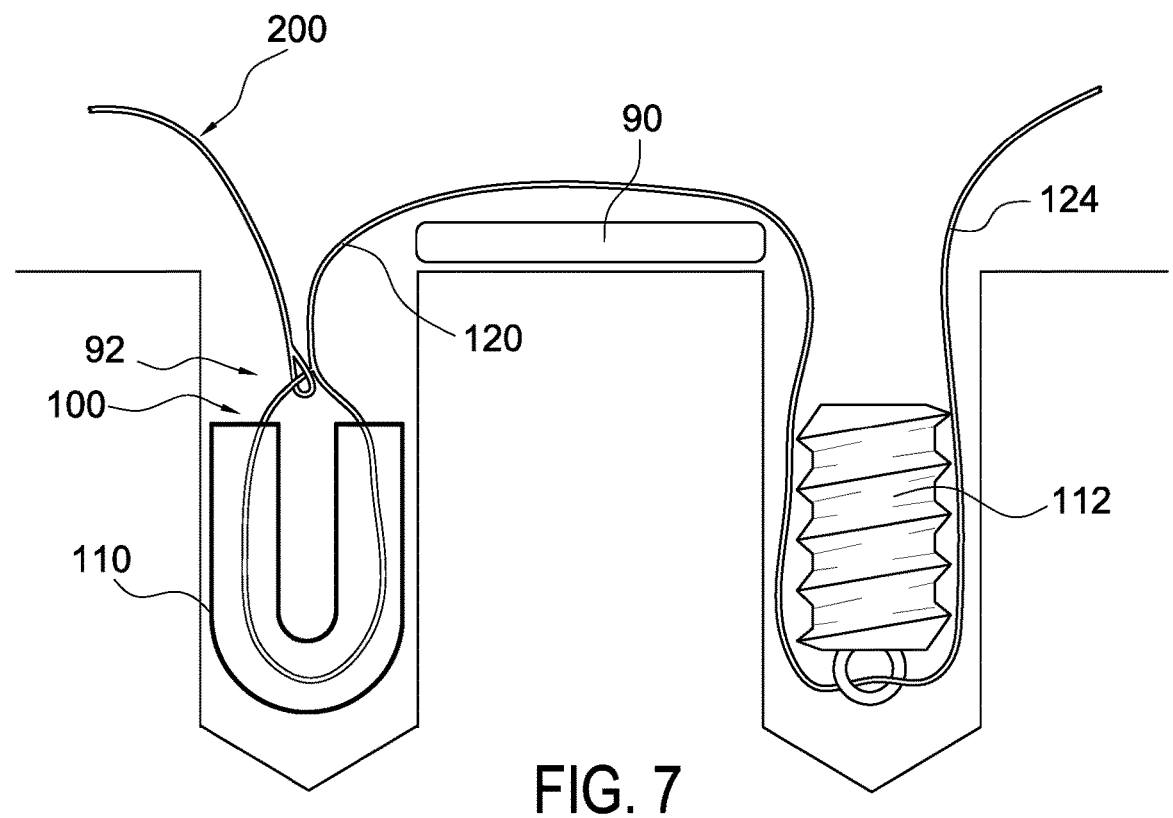
FIGS. 7-9 are each an elevational view of an exemplary surgical construct used in an exemplary method of tissue repair, showing the surgical construct installed in one bone hole and secured to another bone hole.

As seen in FIG. 7, the method of the present disclosure may include the step of adding a second fixation device 112 that is coupled to surgical construct 100. The second fixation device 112 may be attached to the free end 124 of primary repair strand 120 or to a secondary repair strand 200a, 200a', 200b, 200b' coupled to primary repair strand 120. The second fixation device 112 may be installed in a second bone hole 94.

Figure 8:
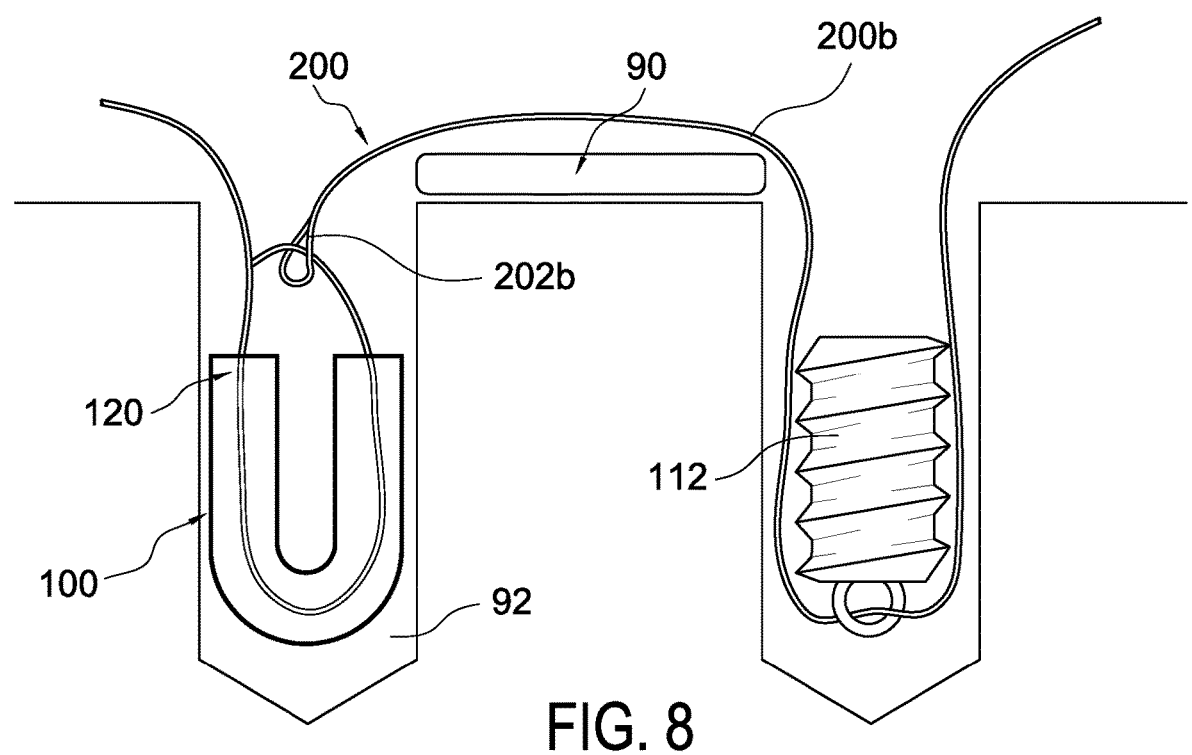

In another example, the secondary repair mechanism 200, such a secondary repair flexible strand 200b, can be coupled to the second fixation device 112 such that the strand 200b extends over the tissue 90, as seen in FIG. 8. The primary repair strand 120 can be left free for use in other parts of the repair and does not have to be coupled to the tissue 90.

Figure 9:
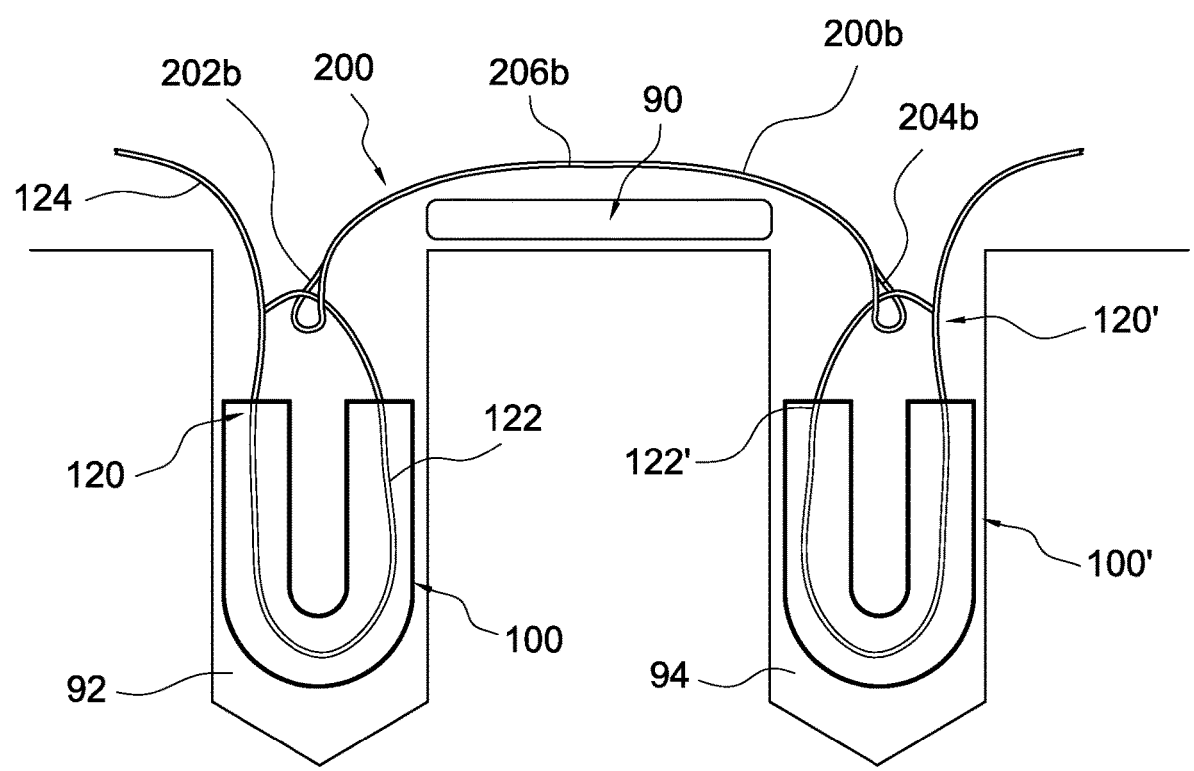

In yet another example, a second surgical construct 100', that also has a primary repair flexible strand 120', may be installed onto the second bone hole 94. The secondary repair flexible strand 200 may be coupled to both the primary repair flexible strand 120 of construct 100 and the primary repair flexible strand 120' of the second construct 100', such that the secondary repair strand 200 extends over the tissue 90, as seen in FIG. 9. For example, the secondary repair flexible strand 200b can be coupled to the primary repair flexible strand 120 of construct 100 via eyelet 202b at one end, as discussed above, and can be coupled to the primary repair flexible strand 120' of the second construct 100', such as at an adjustable loop 122' thereof, by the strand's eyelet 204b at the other end. Alternatively, the sliding secondary repair flexible strand 200a may be coupled to respective segments of each adjustable loop 122 and 122' such that the strand 200a, such as its loop portion 206b, extends over the tissue 90, with the free ends 202a and 204a (FIG. 4a) being tie together. In another alternative, the second surgical construct 100' may also have its own secondary repair flexible strand that is configured to couple with the secondary repair flexible strand 200 of construct 100.

It should be understood that terms such as "lateral," "medial," "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A method of tissue repair, comprising the steps of:
installing a surgical construct in a bone hole, the surgical construct having a fixation device that is preloaded with at least one primary flexible strand;
after installing the surgical construct in the bone hole, coupling at least one secondary flexible strand to the at least one primary flexible strand by extending the at least one primary flexible strand through at least one eyelet of the at least one secondary flexible strand, for subsequent use in repairing the tissue; and
engaging the at least one secondary flexible strand with the tissue only after the step of coupling the at least one secondary flexible strand to the at least one primary flexible strand.

2. The method of claim 1, wherein the at least one primary flexible strand or the at least one secondary flexible strand is configured to pass through or extend around tissue.

3. The method of claim 1, wherein the at least one secondary flexible strand is different than the at least one primary flexible strand.

4. The method of claim 1, wherein the at least one secondary flexible strand has a length that is different than a length of the at least one primary flexible strand.

5. The method of claim 1, wherein the at least one secondary flexible strand is formed of a different material than the at least one primary flexible strand.

6. The method of claim 1, wherein the at least one primary and secondary flexible strands are formed of the same material.

7. The method of claim 1, wherein each of the at least one primary and secondary flexible strands is a suture or suture tape.

8. The method of claim 1, wherein the at least one secondary flexible strand is separable from the at least one primary flexible strand.

9. The method of claim 1, wherein the step of coupling the secondary flexible strand to the at least one primary flexible strand includes slidably coupling the secondary flexible strand around a segment of the at least one primary flexible strand.

10. The method of claim 1, wherein the step of coupling the at least one secondary flexible strand to the at least one primary flexible strand includes extending the at least one primary flexible strand through another eyelet of the at least one secondary flexible strand and each eyelet is located at a respective end of the at least one secondary flexible strand.

11. The method of claim 1, further comprising the step of coupling another secondary flexible strand to the at least one primary flexible strand after the step of installing the surgical construct into the bone hole.

12. The method of claim 1, further comprising the step of coupling a tissue fixation device to the at least one secondary flexible strand.

13. The method of claim 1, further comprising the step of extending the at least one secondary flexible strand through or around tissue and then tying free ends of the at least one secondary flexible strand.

14. The method of claim 13, further comprising the step of coupling a tissue fixation device to the free ends of the at least one secondary flexible strand.

15. The method of claim 14, wherein the tissue fixation device is a button and the free ends of the at least one secondary flexible strand extend around or through apertures of the button.

16. The method of claim 1, further comprising the step of coupling at least one of the at least one primary or secondary flexible strands to a second fixation device installed in another bone hole.

17. The method of claim 1, wherein the fixation device of the surgical construct is a soft anchor.

18. A method of tissue repair, comprising the steps of:
installing a surgical construct in a bone hole, the surgical construct having a fixation device that is preloaded with at least one primary flexible strand;
creating a tensionable adjustable loop in the at least one primary flexible strand; and
after installing the surgical construct in the bone hole, coupling at least one secondary flexible strand to the at least one primary flexible strand for subsequent use in repairing the tissue,
wherein the at least one secondary flexible strand is configured to engage the tissue after the step of coupling the at least one secondary flexible strand to the at least one primary flexible strand, and
wherein the step of coupling the at least one secondary flexible strand to the at least one primary flexible strand occurs before the step of creating the tensionable adjustable loop in the at least one primary flexible strand.

19. The method of claim 18, wherein the at least one primary flexible strand or the secondary flexible strand is configured to pass through or extend around tissue.

20. The method of claim 18, wherein the step of coupling the at least one secondary flexible strand to the at least one primary flexible strand occurs after the step of creating the tensionable adjustable loop in the at least one primary flexible strand.

21. The method of claim 18, further comprising the step of pulling at least a portion of the at least one secondary flexible strand into the bone hole.

22. The method of claim 18, further comprising the step of anchoring the surgical construct to another bone hole.

23. The method of claim 18, further comprising the step of selecting the at least one secondary flexible strand from one of a sliding suture or suture tape slidably coupled to the at least one primary flexible strand or a suture or suture tape with an eyelet for coupling to the at least one primary flexible strand.

24. The method of claim 18, further comprising the step of coupling another secondary flexible strand to the at least one primary flexible strand after the step of installing the surgical construct into the bone hole.

25. The method of claim 18, further comprising the step of coupling either the at least one primary or secondary flexible strand to a second fixation device installed in another bone hole.

26. The method of claim 18, further comprising the step of coupling the at least one secondary flexible strand to a second surgical construct installed in another bone hole.

27. The method of claim 18, wherein the at least one secondary flexible strand is separable from the primary strand.

28. The method of claim 18, further comprising the step of coupling the at least one secondary flexible strand to tissue.

29. The method of claim 28, wherein the step of coupling the at least one secondary flexible strand to tissue includes coupling a tissue fixation device to the at least one secondary flexible strand.

30. A method of tissue repair, comprising the steps of:
installing a surgical construct in a bone hole, the surgical construct having a fixation device that is preloaded with at least one primary flexible strand;
creating a tensionable adjustable loop in the at least one primary flexible strand; and
after installing the surgical construct in the bone hole, coupling at least one secondary flexible strand to the at least one primary flexible strand for subsequent use in repairing the tissue,
wherein the step of coupling the at least one secondary flexible strand to the at least one primary flexible strand occurs before the step of creating the tensionable adjustable loop in the at least one primary flexible strand.

31. A method of tissue repair, comprising the steps of:
installing a surgical construct in a bone hole, the surgical construct having a fixation device that is preloaded with at least one primary flexible strand;
after installing the surgical construct in the bone hole, coupling at least one secondary flexible strand to the at least one primary flexible strand, for subsequent use in repairing the tissue;
engaging the at least one secondary flexible strand with the tissue only after the step of coupling the at least one secondary flexible strand to the at least one primary flexible strand; and coupling another secondary flexible strand to the at least one primary flexible strand after the step of installing the surgical construct into the bone hole.

32. A method of tissue repair, comprising the steps of:

installing a surgical construct in a bone hole, the surgical construct having a fixation device that is preloaded with at least one primary flexible strand;

after installing the surgical construct in the bone hole, coupling at least one secondary flexible strand to the at least one primary flexible strand, for subsequent use in repairing the tissue;

engaging the at least one secondary flexible strand with the tissue only after the step of coupling the at least one secondary flexible strand to the at least one primary flexible strand; and extending the at least one secondary flexible strand through or around tissue and then tying free ends of the at least one secondary flexible strand.

33. A method of tissue repair, comprising the steps of:

installing a surgical construct in a bone hole, the surgical construct having a fixation device that is preloaded with at least one primary flexible strand;

after installing the surgical construct in the bone hole, coupling at least one secondary flexible strand to the at least one primary flexible strand, for subsequent use in repairing the tissue;

engaging the at least one secondary flexible strand with the tissue only after the step of coupling the at least one secondary flexible strand to the at least one primary flexible strand; and coupling at least one of the at least one primary or secondary flexible strands to a second fixation device installed in another bone hole.

* * * * *